(12) United States Patent
Wang

(10) Patent No.: US 10,251,967 B1
(45) Date of Patent: Apr. 9, 2019

(54) AROMATHERAPY CANDLE WATERLAMP

(71) Applicant: Hua-Cheng Pan, Tainan (TW)

(72) Inventor: Chih-Liang Wang, Tainan (TW)

(73) Assignee: Hua-Cheng Pan, Tainan (TW)

( * ) Notice: Subject to any disclaimer, the term of this patent is extended or adjusted under 35 U.S.C. 154(b) by 0 days.

(21) Appl. No.: 15/889,230

(22) Filed: Feb. 6, 2018

(51) Int. Cl.
*A61L 9/03* (2006.01)
*F21S 10/04* (2006.01)

(52) U.S. Cl.
CPC ............... *A61L 9/03* (2013.01); *F21S 10/04* (2013.01); *A61L 2209/12* (2013.01)

(58) Field of Classification Search
CPC ......... A61L 9/03; A61L 2209/12; F21S 10/04
See application file for complete search history.

(56) References Cited

U.S. PATENT DOCUMENTS

| | | | | |
|---|---|---|---|---|
| 6,638,060 B1 * | 10/2003 | Rivard | ....................... | A61L 9/03 362/161 |
| 7,784,959 B2 * | 8/2010 | Yang | ..................... | F21S 10/002 362/101 |
| 7,798,673 B2 * | 9/2010 | Yang | ..................... | F21S 10/002 362/101 |
| 7,934,845 B2 * | 5/2011 | Yang | ....................... | F21S 6/001 362/101 |
| 8,628,208 B1 * | 1/2014 | Yang | ..................... | F21S 10/043 362/161 |
| 9,163,795 B2 * | 10/2015 | Yang | ....................... | F21S 6/001 |
| 2004/0068781 A1 * | 4/2004 | Hill | ........................ | A01M 1/02 4/222 |
| 2005/0030747 A1 * | 2/2005 | Bogdal | .................... | A61L 9/03 362/253 |
| 2013/0265743 A1 * | 10/2013 | Lee | ..................... | F21V 33/0004 362/96 |
| 2015/0338087 A1 * | 11/2015 | Fang | ....................... | F24F 3/056 362/96 |

* cited by examiner

*Primary Examiner* — Mary Ellen Bowman
(74) *Attorney, Agent, or Firm* — Leong C. Lei

(57) ABSTRACT

An aromatherapy candle waterlamp including: a waterlamp main body, a container, a bottom case and a top-cover. The main body is filled with a flowing liquid and set a hollow channel. The container is set in the top of the main body and the bottom case is fixedly connected with the bottom of the main body. A control circuit, a power module for supplying power, a light source, an electricity conductive wire, and an electric heating piece are set inside the bottom case. The light source irradiates toward the bottom of the main body. The electricity conductive wire is partially set through the hollow channel of the waterlamp main body and is electrically connected with an electric heating piece. The top-cover having a three-dimensional shape is set for correspondingly covering the top of the main body and is alternately set with a plurality of through holes.

5 Claims, 7 Drawing Sheets

AROMATHERAPY CANDLE WATERLAMP

(a) TECHNICAL FIELD OF THE INVENTION

The present invention relates to a candle, especially relates to one kind of the electronic candle structure which is used in the visual environmental furnish and decoration and has the aromatherapy function.

(b) DESCRIPTION OF THE PRIOR ART

There are many types of electronic candles available on the market. They are usually simple luminaries with a candle shape and are simply used to provide lighting, such that they lack the aesthetic appearance, interest, taste and the easiness to create the atmosphere.

Therefore, based on many years of research experience in the field of furnish and decoration accessories, the inventor of the present invention has designed and invented various electronic waterlamp candles with dynamic effects for furnish and decoration, such as U.S. Pat. Nos. 7,934,845; 7,784,959; and 7,798,673.

However, this electronic candle itself shows a visual feeling of creating an indoor atmosphere, which cannot further have other functional changes and is gradually unable to attract the attention of the consumers for the new and changing society.

Therefore, how to provide an electronic candle design with an innovative structure to further enhance its added value and taste is one of the most important topics at present.

SUMMARY OF THE INVENTION

The main purpose of the present invention is to enhance the added value of conventional electronic candle decorations with other functional changes.

Therefore, the present invention provides an aromatherapy candle waterlamp, which mainly includes: a waterlamp main body with a hollow channel in the axial direction and a groove at the top for communicating with the hollow channel; wherein the waterlamp main body is hollow and internally filled with flowing liquid; a container set in the groove of the waterlamp main body; wherein the container is made of heat-resistant material; a bottom case opened upwardly and fixedly connected with the bottom of the waterlamp main body; wherein a control circuit, a power module for supplying power, at least one light source, an electricity conductive wire, and an electric heating piece are set inside the bottom case; wherein the light source irradiates toward the bottom of the waterlamp main body, which the light source and the electricity conductive wire are electrically connected with the control circuit respectively; wherein the electricity conductive wire is partially set through the hollow channel of the waterlamp main body and is electrically connected to the electric heating piece, which the electric heating piece is correspondingly set below the container; and a top-cover which is a three-dimensional shape for correspondingly covering the top of the waterlamp main body, wherein the top-cover is alternately set with a plurality of through holes corresponding to the upside of the container.

Accordingly, the present invention can be used as an ornament for decorating the environment, and at the same time, the essential oil or aromatherapy can be dripped into the container; so that the electric heating piece set at the bottom of the container can heat the container to make the fragrance in the container spread into the environment.

DETAILED DESCRIPTION OF THE PREFERRED EMBODIMENTS

Figure 1:
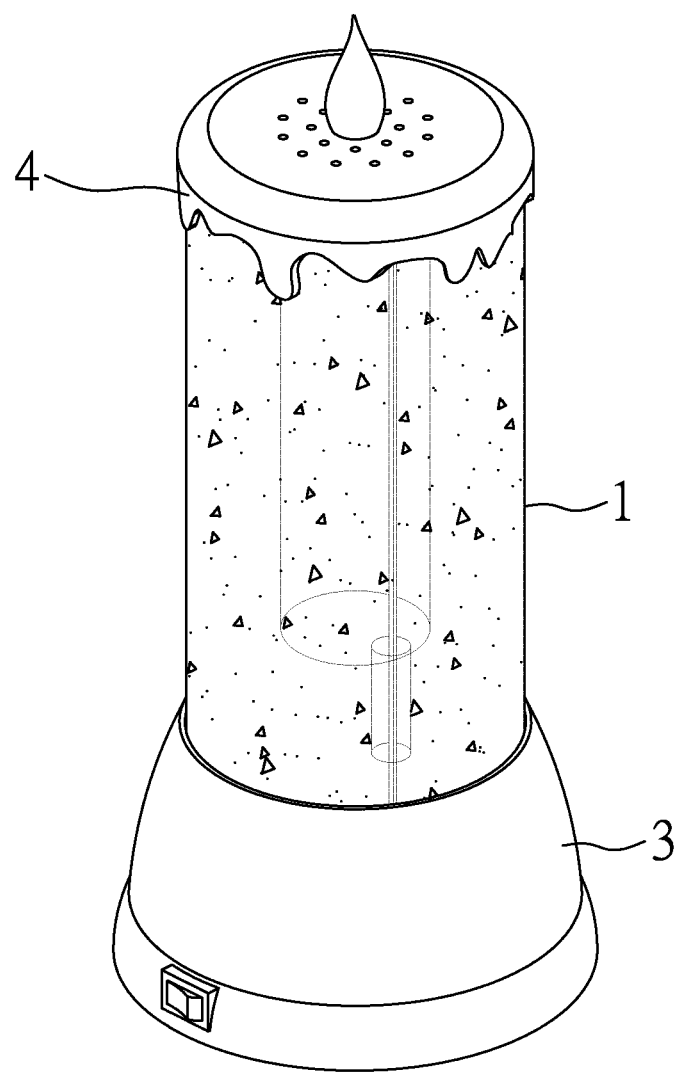
FIG. 1 is a perspective view according to the present invention.
Figure 2:
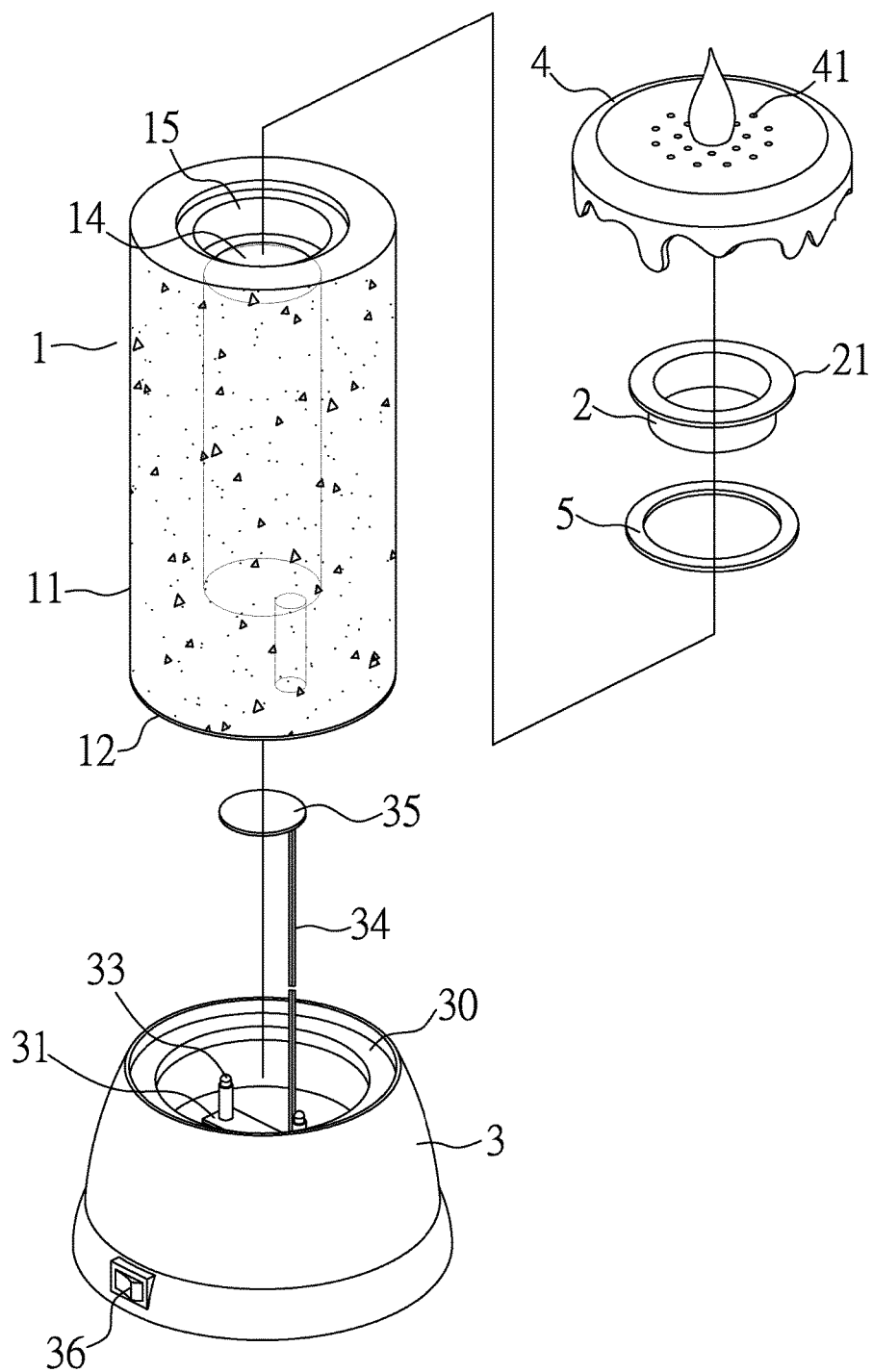
FIG. 2 is a decomposition schematic diagram according to the present invention.
Figure 3:
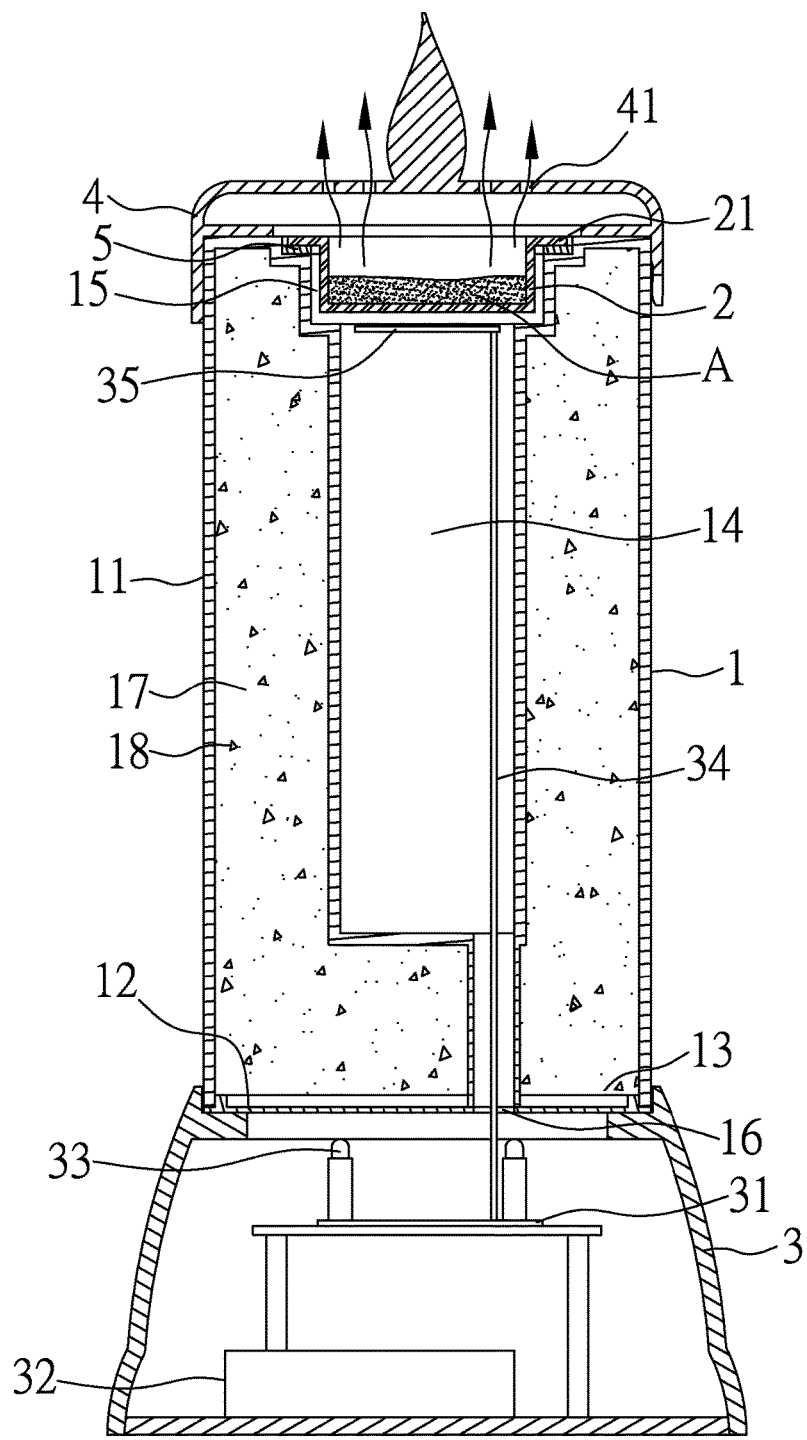
FIG. 3 is a decomposition schematic diagram according to the present invention.

The following will be described with reference to the related figures, which illustrate an aromatherapy candle waterlamp according to a preferred embodiment of the present invention. As shown in FIG. 1 to FIG. 3, the separable recharge nightlight of the present invention mainly comprises a waterlamp main body (1), a container (2), a bottom case (3) and a top-cover (4), wherein: the waterlamp main body (1) comprises a transparent shell body (11) and a bottom cover 12.

The shell body (11) has a hollow and cylindrical shape with a downward opening (13), and the shell body (11) is set a hollow channel (14) axially penetrating the shell body (11) and a groove (15) which is connected with the hollow channel (14) and formed in the top of the shell body (11), wherein a bottom-cover (12) is used to close the opening (13). And, a through hole (16) is formed corresponding to the hollow channel (14). The bottom-cover (12) combines with the shell body (11) define an accommodating space (17) to fill with the fluid liquid, wherein a plurality of sequins (18) is further incorporated into the liquid in this embodiment.

The container (2) is circularly set with an edge-portion (21) which is matched to the groove (15) of the waterlamp main body (1), and the container (2) is made of the heat-resistant materials, such as: stainless steel, aluminum, ceramics, . . . and so on.

The bottom case (3) is upwardly connected with the opening (30) and is fixedly connected to the bottom of the waterlamp main body (1). The bottom case (3) is set with a control circuit (31), a power module (32) for supplying the electricity, at least one light source (33), an electricity conductive wire (34) and an electric heating piece (35) inside. The light source (33) is an LED lamp or a general light bulb (such as a tungsten bulb) which emits light towards the bottom of the waterlamp main body (1). The light source (33) and the electricity conductive wire (34) are electrically connected with the control circuit (31) respectively. The control circuit (31) is a design of a general electronic substrate and is not covered by the scope of the application of the present invention, therefore it will not be further described here. The electricity conductive wire (34) is partially exposed by the opening 30 of the bottom case (3) and is set through the hollow channel (14) of the waterlamp main body (1), and is electrically connected to the electric heating piece (35); wherein the electric heating piece (35) is correspondingly set below the container (2). In this embodiment, the power module (32) is a battery and it further has a power switch (36) for turning on and off the power module (32).

The top-cover (4) is a three-dimensional shape of a candlelight connected with the melting-candle, which correspondingly covers the top of the waterlamp main body (1), and the top-cover (4) is alternately set with a plurality of through holes (41) corresponding to the upside of the container (2).

Moreover, a heat insulation ring (5) is set between the container (2) and the waterlamp main body (1) to block the temperature of the container (2) and prevent the waterlamp main body (1) from being damaged.

Accordingly, the light source (33) irradiates toward the inside of the waterlamp main body (1), and the control circuit (31) can control the color conversion and the flickering frequency of the light source (33). Its light is refracted through the liquid and the sequins (18) to form a dazzling visual feeling, and the user can place the fragrance product (A), for example, essential oils, aromatherapy fragrances, . . . etc. in the container (2) to be indirectly heated by the electric heating piece (35) set below the container (2) to spread the fragrance into the environment at the same time.

Figure 4:
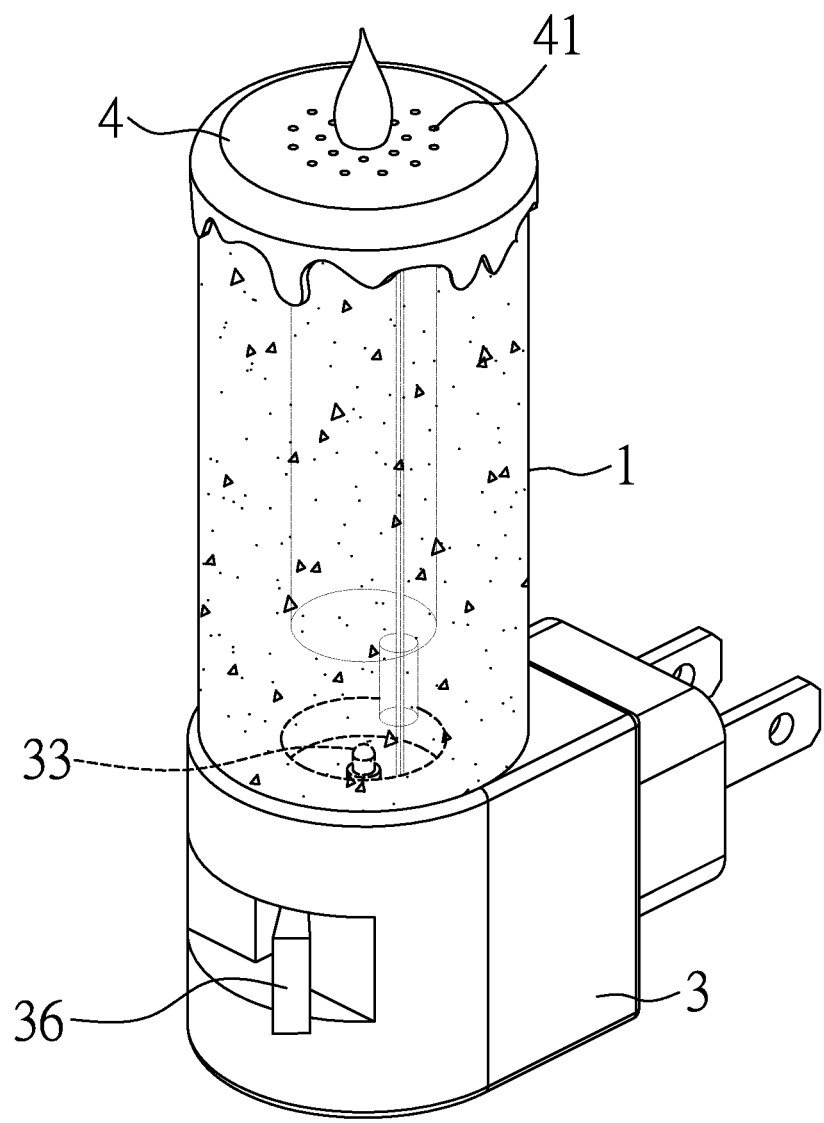
FIG. 4 is a schematic diagram in the using status according to the present invention.

Please continue to cooperate with FIG. 4, which shows the embodiment of the present invention for a small nightlight, the bottom case (3) is a nightlight holder, and its power module (32) is a mains supply plug, wherein the power module (32) is set in one side of the bottom case (3) and is electrically connected to the control circuit (31).

When the bottom case (3) is plugged into a mains supply socket, the present embodiment forms a small-sized ambient light and can simultaneously perform the aromatherapy function, too.

Figure 5:
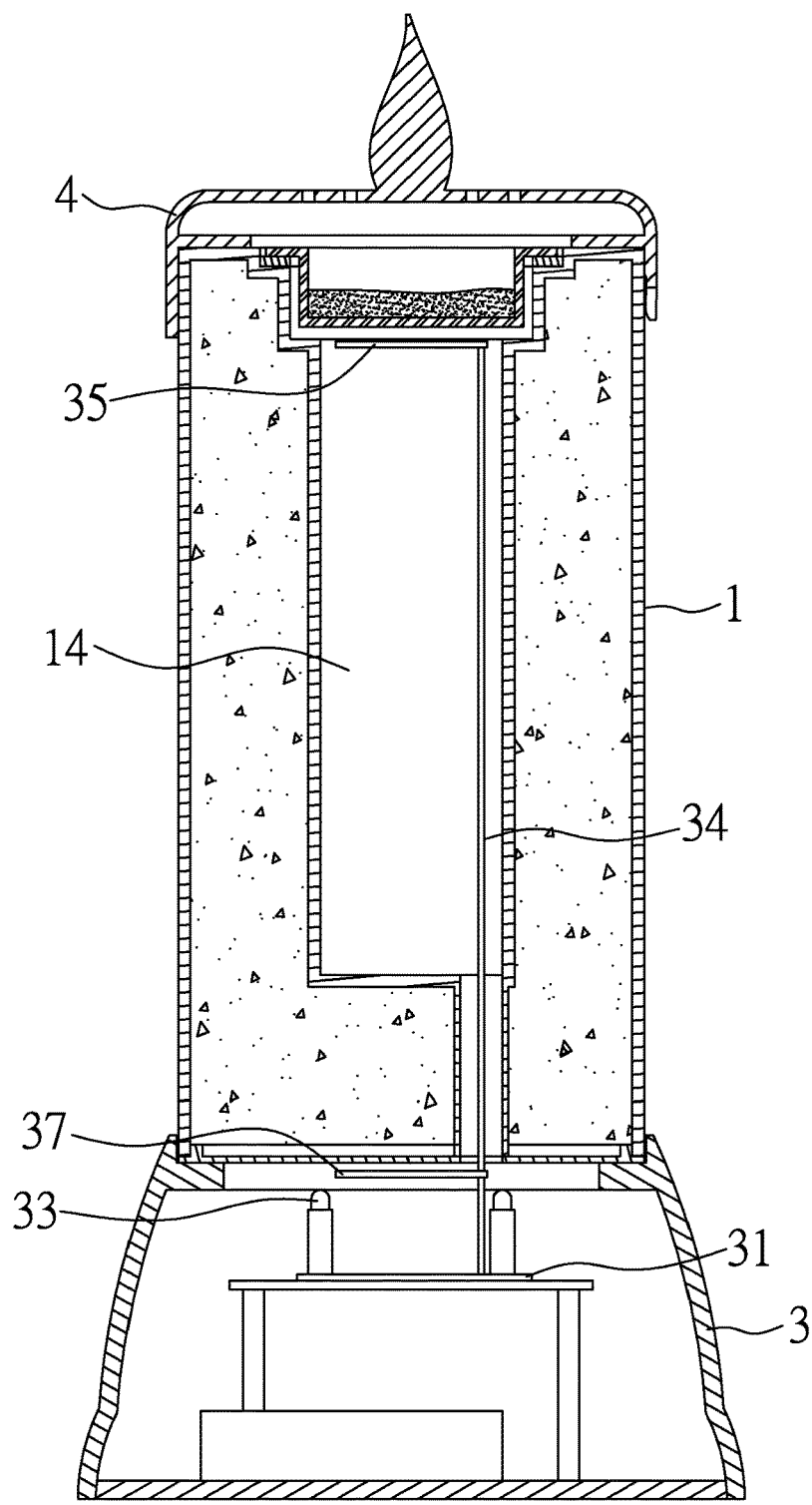
FIG. 5 is a schematic diagram in the using status according to the present invention.

Continuously, as shown in FIG. 5, in order to make the liquid inside the water lamp main body (1) flow by itself, the liquid is a low-boiling liquid, such as the methylene chloride.

The control circuit (31) corresponding to the bottom of the waterlamp main body (1) is set with a heating stuff (37) which can generate heat by the impedance effect of the electricity, wherein the heating stuff (37) can be one of the general resistor, cement resistor, heating wire, or electric heating piece. When the power is turned on, the heating stuff (37) will generate heat by the electricity and the light source (33) will produce light to irradiate the low-boiling liquid in the waterlamp main body (1), which will make the low-boiling liquid flow by the thermal energy generated from the underside; and thus make this embodiment has a micro-dynamic effect.

In addition, when the light source (33) is a tungsten bulb, the heat source generated by the electricity may also cause the low-boiling liquid to flow.

Figure 6:
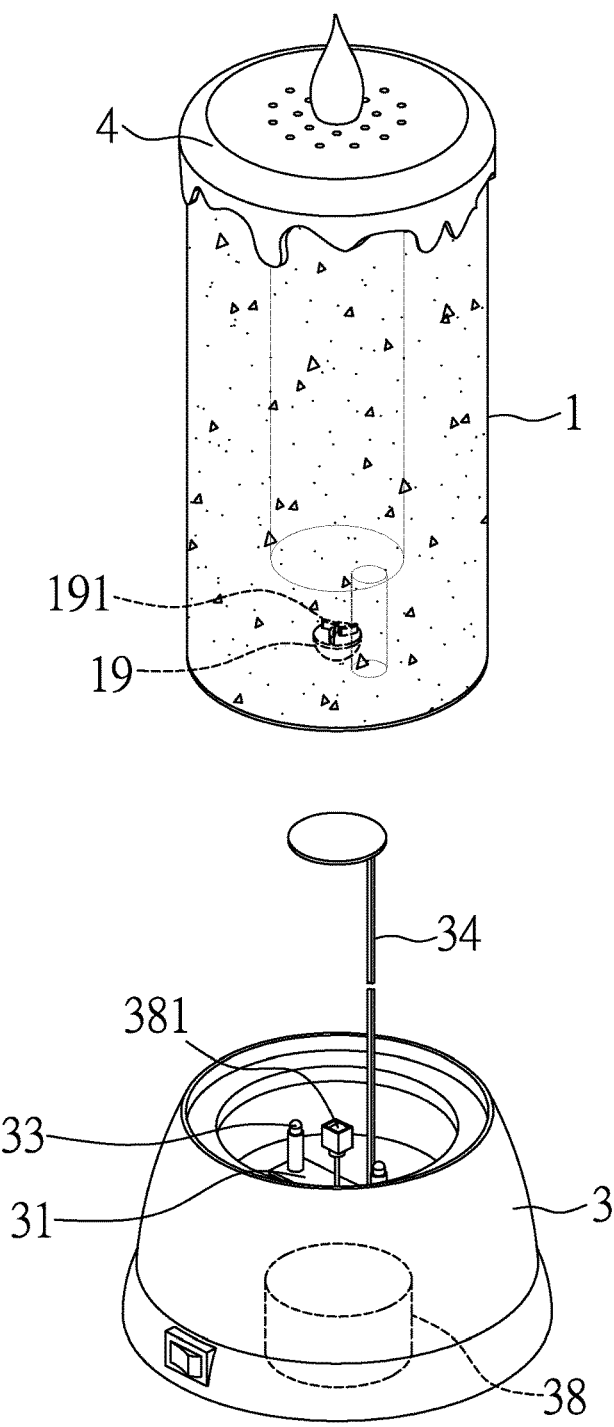
FIG. 6 is a decomposition schematic diagram according to the present invention.
Figure 7:
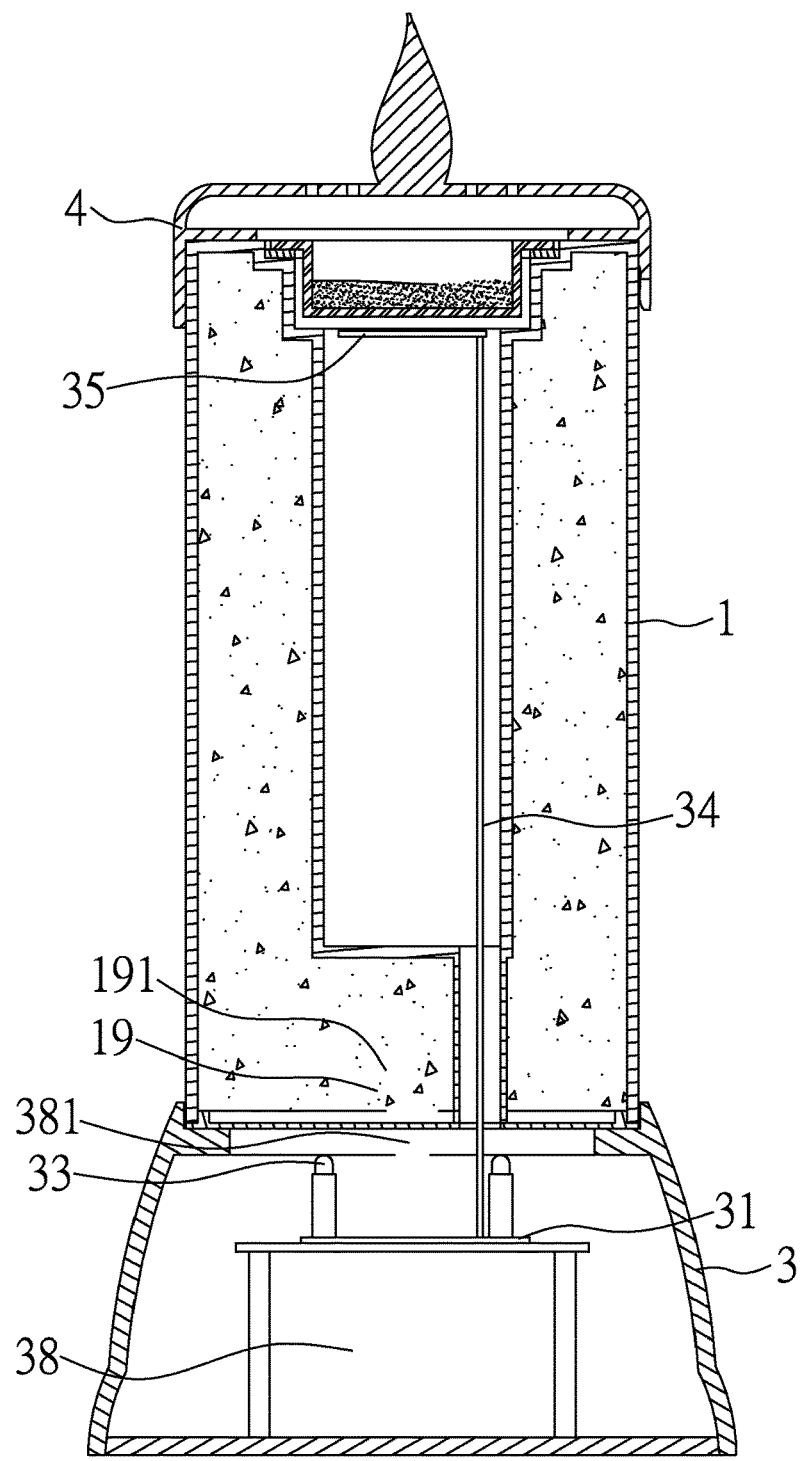
FIG. 7 is a schematic diagram in the using status according to the present invention.

Continuously, as shown in FIG. 6 and FIG. 7, in the present embodiment, a magnetic actuator (19) is set on the inner bottom of the waterlamp main body (1). The top of the magnetic actuator (19) is provided with a plurality of fins (191) in a radial arrangement, and the bottom case (3) is set with a motor (38). A magnetism piece (381) of the motor (38) is set corresponding to the bottom of the waterlamp main body (1) to correspondingly attract the magnetic actuator (19) by the magnetism.

When the motor (38) rotates, the magnetism piece (381) is controlled to rotate and the magnetic actuator (19) is pulled and rotated by the magnetic attraction, so that the interior liquid of the waterlamp main body (1) will flow owing to the toggle of the magnetism inductive piece (19) and the fins (191).

To sum up, in addition to being used as the ambient lighting and decoration, the present invention also has the function of aromatherapy. In fact, present invention enhances the added value of the electronic candle decorations and enhances the product competitiveness.

However, the above description is only a preferred embodiment of the present invention and is not intended to limit the characteristics of the present invention. Any attempt to create a principle again through the use of the technical means related to the present invention remains the creative domain of the present invention. Therefore, the illustrations in the present invention and the statements contained herein are not intended to limit the scope of the present invention. Any equivalent changes and modifications made by those skilled in the art without departing from the spirit and scope of the present invention should be covered by the present invention and within the scope of the patent of the present invention, which is reasonable.

I claim:

1. An aromatherapy candle waterlamp, which comprises:
  a waterlamp main body set with a hollow channel in the axial direction and a groove set in a top and communicating with the hollow channel; wherein the waterlamp main body is hollow and internally filled with a flowing liquid;
  a container set in the groove of the waterlamp main body; wherein the container is made of a heat-resistant material;
  a bottom case set upwardly opened and fixedly connected with a bottom of the waterlamp main body; wherein a control circuit, a power module for supplying power, at least one light source, an electricity conductive wire, and an electric heating piece are set inside the bottom case;
  wherein the light source irradiates toward the bottom of the waterlamp main body, and the light source and the electricity conductive wire are electrically connected with the control circuit respectively;
  wherein the electricity conductive wire is partially set through the hollow channel of the waterlamp main body and is electrically connected with the electric heating piece, which is set below the container; and
  a top-cover having a three-dimensional shape set for covering the top of the waterlamp main body; wherein the top-cover is set with a plurality of through holes that are separate from each other and are formed in a portion of the top-cover corresponding to the container;
  wherein the flowing liquid inside the water lamp main body is a low-boiling liquid and a heating stuff is connected to the control circuit and is set corresponding to the bottom of the waterlamp main body; and
  wherein the control circuit controls the electric heating piece and the heating stuff to respectively generate first and second amounts of heat toward the container and the bottom and the low-boiling liquid of the waterlamp main body.

2. The aromatherapy candle waterlamp according to claim 1, wherein a heat insulation ring is set between the container and the waterlamp main body.

3. The aromatherapy candle waterlamp according to claim 1, wherein the bottom case is a nightlight holder and the power module is a mains supply plug.

4. The aromatherapy candle waterlamp according to claim 1, wherein the heating stuff is one of a general resistor, a cement resistor, a heating wire, and an electric heating piece.

5. The aromatherapy candle waterlamp according to claim 1, wherein a magnetic actuator is set on the inner bottom of the waterlamp main body and a motor is set in the bottom case, wherein a magnetism piece of the motor is set correspondingly to the bottom of the waterlamp main body to correspondingly attract the magnetic actuator by the magnetism.

* * * * *